Figure 1:
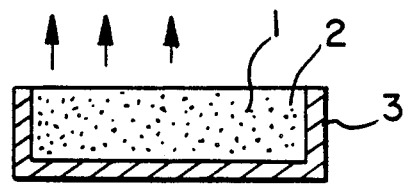

United States Patent [19]

Nagy et al.

[11] Patent Number: 4,997,655
[45] Date of Patent: Mar. 5, 1991

[54] PHARMACEUTICAL FORMULATION ENSURING THE TRANSDERMAL ABSORPTION OF THE ACTIVE INGREDIENT AND PROCESS FOR PREPARING SAME

[75] Inventors: József Nagy; Ferenc Salamon; Odön Wagner, all of Budapest, Hungary

[73] Assignee: Biogal Gyogyszergyar, Budapest, Hungary

[21] Appl. No.: 315,894

[22] PCT Filed: Jun. 22, 1988

[86] PCT No.: PCT/HU88/00044
§ 371 Date: Feb. 17, 1989
§ 102(e) Date: Feb. 17, 1989

[87] PCT Pub. No.: WO88/10111
PCT Pub. Date: Dec. 29, 1988

[30] Foreign Application Priority Data

Jun. 22, 1987 [HU] Hungary ............................. 2822/87

[51] Int. Cl.$^5$ ............................................. A61F 13/00
[52] U.S. Cl. .................................... 424/448; 424/449
[58] Field of Search ....................... 424/448, 449, 443

[56] References Cited

U.S. PATENT DOCUMENTS

| | | | |
|---|---|---|---|
| 3,598,122 | 8/1971 | Zaffaroni | 424/448 X |
| 3,742,951 | 7/1973 | Zaffaroni | 424/448 X |
| 4,031,894 | 6/1977 | Urquhart et al. | 424/448 |
| 4,060,084 | 11/1977 | Chandrasekaran et al. | 424/448 |
| 4,191,741 | 3/1980 | Hudson et al. | 128/260 |
| 4,341,759 | 7/1982 | Boggentoft et al. | 424/489 X |
| 4,421,737 | 12/1983 | Ito et al. | 424/448 X |
| 4,460,371 | 7/1984 | Abber | 424/448 |
| 4,615,699 | 10/1986 | Gale et al. | 424/448 |
| 4,661,105 | 4/1987 | Gale | 604/897 |
| 4,690,683 | 9/1987 | Chien et al. | 424/448 |
| 4,865,848 | 9/1989 | Cheng et al. | 424/448 X |

*Primary Examiner*—Thurman K. Page
*Attorney, Agent, or Firm*—Michael N. Meller

[57] ABSTRACT

The invention relates to a multilayer pharmaceutical formulation containing layers with various active ingredient content, a water-impermeable layer applied thereon and an adhesive layer ensuring the fixation to the body surface of the pharmaceutical formulation, which comprises: a silicone rubber layer directly contacting with the skin surface and ensuring the zero order kinetics of the dissolution of the active ingredient; as well as a multilaminated silicone rubber matrix comprising one or more layers(s) with various active ingredient content.

8 Claims, 3 Drawing Sheets

PHARMACEUTICAL FORMULATION ENSURING THE TRANSDERMAL ABSORPTION OF THE ACTIVE INGREDIENT AND PROCESS FOR PREPARING SAME

This invention relates to a multilayer pharmaceutical formulation which, when put onto the skin, ensures the protracted (suitably lasting about 18 to 24 hours) absorption with so called zero order kinetics of the incorporated active ingredient.

According to an other aspect of the invention, there is provided a process for the preparation of these multilayer pharmaceutical formulations.

There are known pharmaceutical formulations in the prior art which ensure the transdermal absorption of the incorporated active ingredient content. The polymeric matrix of a nitroglycerin-containing composition commercialized by Key Pharmaceuticals Inc. under the trade mark Nitro-Dur contains 2 to 60% of glycerol, 2 to 15% of polyvinyl alcohol and 2 to 10% of a water-soluble polymer, e.g. PVP (see the U.S. Pat. No. 4,466,953). This polymeric matrix ensures the suitable dissolution kinetics of the active ingredient.

The Transderm compositions produced by Alza Co. are pharmaceutical formulations consisting of four layers which contain the active ingredient in an admixture with an ointment based on a silicone; the dissolution of the active ingredient is regulated by a non-porous membrane prepared from ethylene/vinyl acetate. For ensuring the initial dose, the adhesive layer of this composition also contains 8% of active ingredient.

The compositions produced by Searle Co., e.g. Nitrodisc ®, are prepared in such a way that the active ingredient is suspended in the solution of a water-soluble polymer and the suspension obtained is mixed into a silicone polymer; thereafter, the cross-linking is carried out and finally, a specific membrane layer is also applied in order to regulate the dissolution of the active ingredient (see the U.S. Pat. No. 3,946,106).

The structure of the Nitroderm-TTS compositions of Ciba-Geigy AG is practically identical to that of the Transderm compositions.

Summing up, the structure of the formulations known up to the present are as follows.

(1) Matrix system (FIG. 1)
  1. diffusion-regulating polymeric matrix (gel, ointment);
  2. solid active ingredient;
  3. impermeable polymeric layer. [Example: Nitro-Dur (Key Pharm.)]

Figure 2:
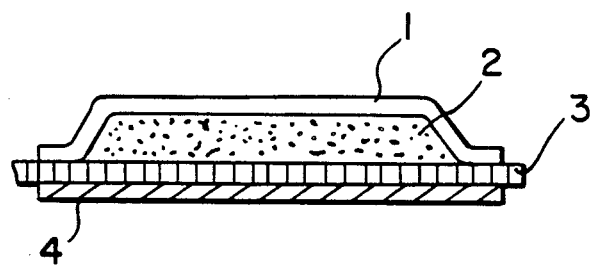

(2) Layered system (FIG. 2)
  1. protective foil;
  2. ointment (gel) containing active ingredient;
  3. dissolution-regulating membrane;
  4. adhesive layer containing the active ingredient. [Example: Transderm-Nitro (Alza Co.)]

Figure 3:
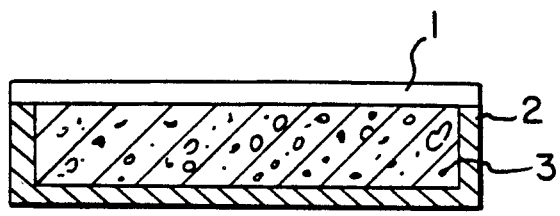

(3) Microsealed system (FIG. 3)
  1. dissolution-regulating polymeric membrane;
  2. aqueous polymeric drops containing an active ingredient suspension;
  3. polymeric matrix (based on a silicone);
  4. impermeable polymeric layer. [Example: Nitrodisc ® (Searle)]

Figure 4:
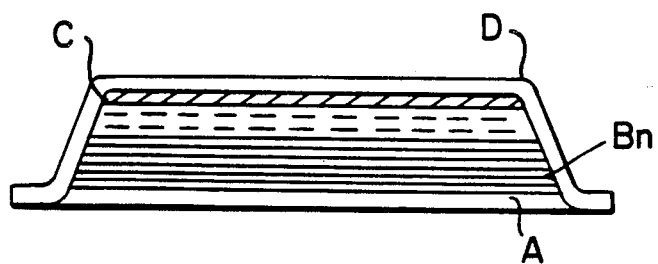
Figure 5:
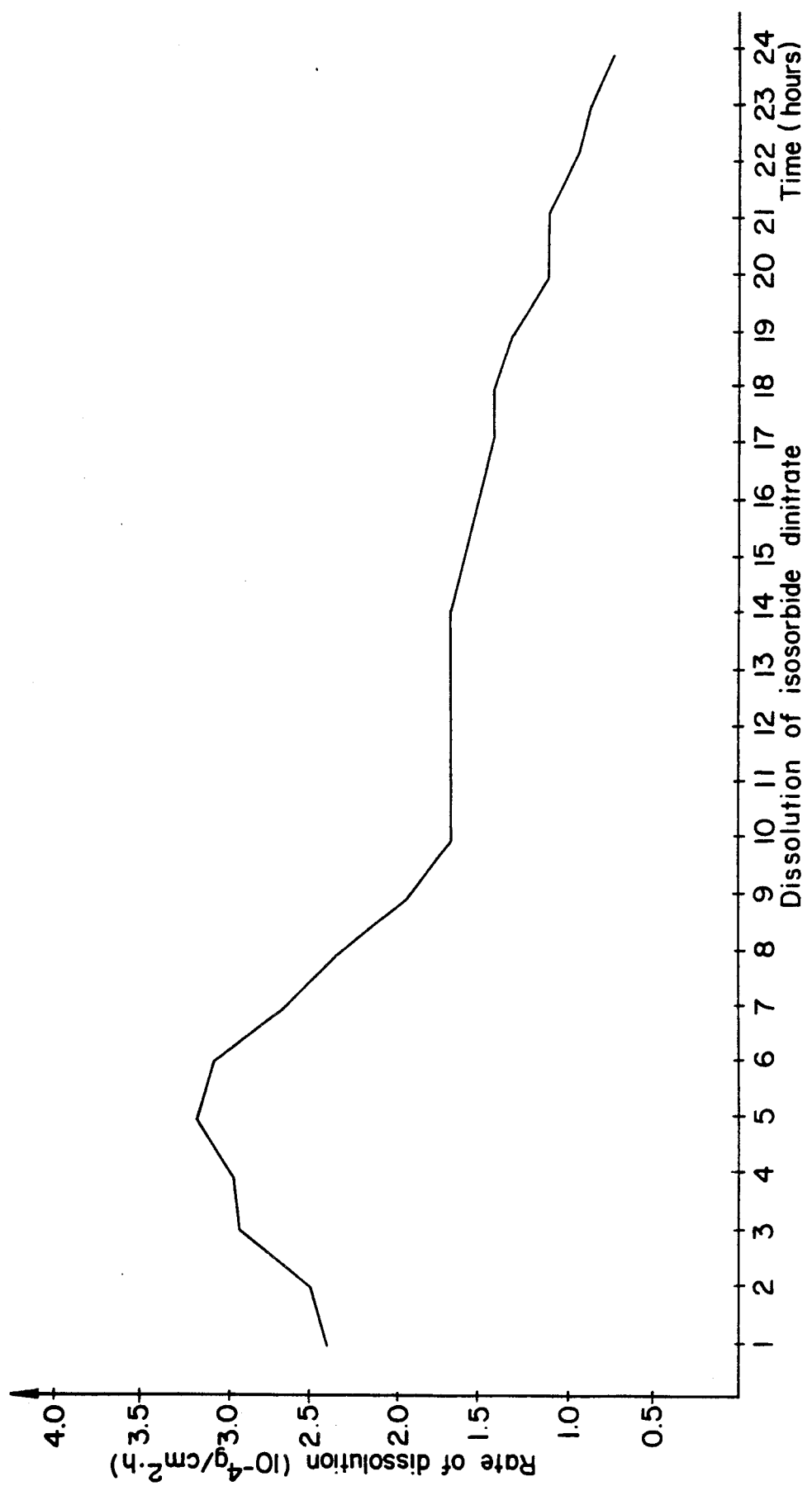
Figure 6:
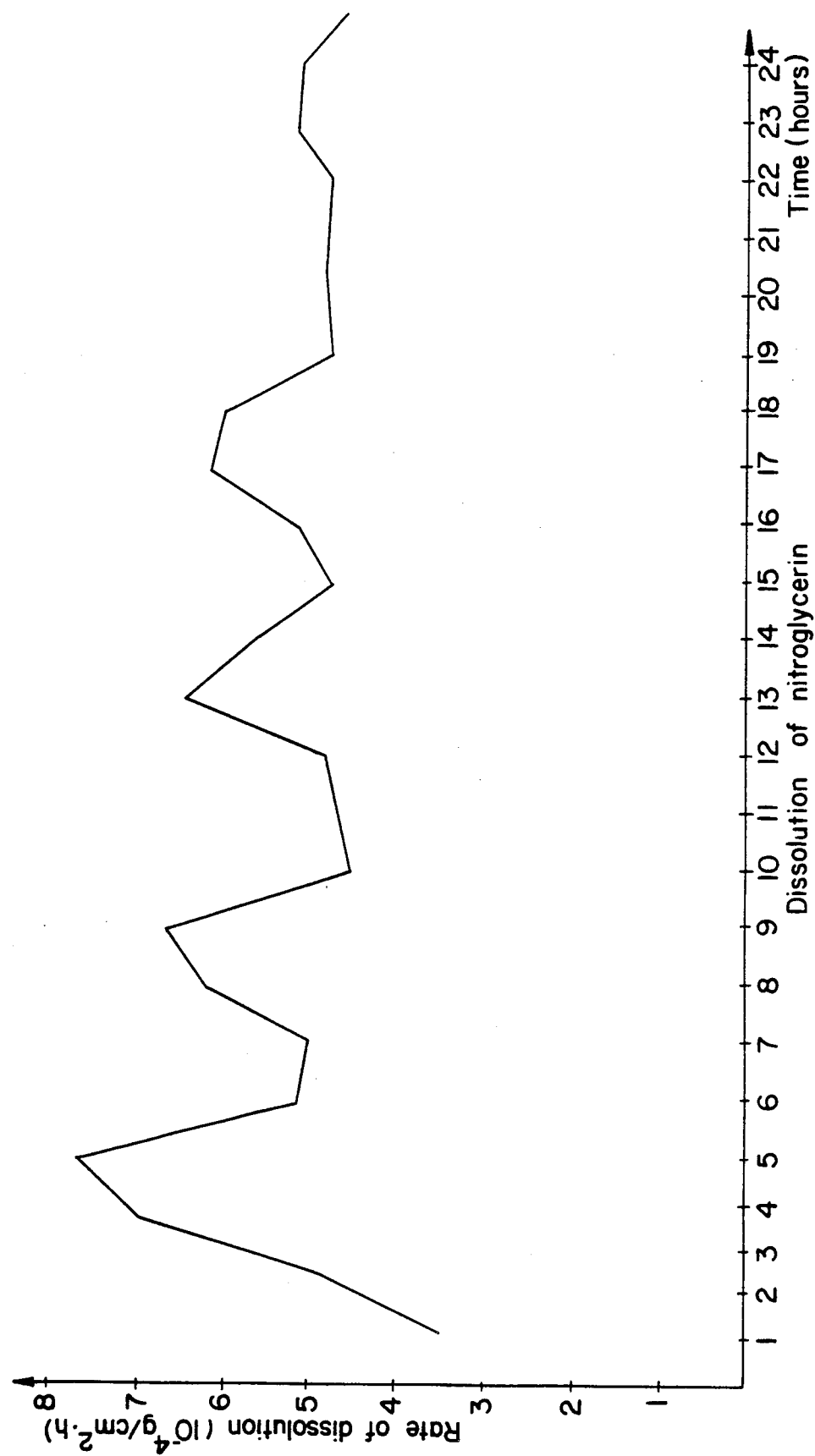

The pharmaceutical formulation according to the invention is a bilayer or multilayer system with a structure illustrated in FIG. 4, wherein A is a silicone rubber layer ensuring the dissolution with zero order kinetics of the active ingredient;

$B_n$ is a multilaminated silicone rubber matrix involving layers (n=1 to 6) with various active ingredient content;

C is an aluminum foil or other suitable, water-impermeable foil layer; and

D is an adhesive layer providing the fixation of the formulation to the body surface.

The layers A and $B_n$ of the pharmaceutical formulation according to the invention are prepared by a catalytic (protolytic) polycondensation or polyaddition process, using one- or two-component silicone rubber basic material. The layers A and $B_n$ mentioned above can be prepared in various thicknesses (0.1 to 3 mm): by the catalytic polycondensation of various alkyl-polysiloxane-$\alpha,\omega$-diols (suitably methylpolysiloxane-$\alpha,\omega$-diols having a low molecular weight (M=500 to 100,000) and/or higher molecular weight (M=100,000 to 20,000,000); or by the catalytic addition of polysiloxane polymers containing various alkyl ($C_nH_{2n+1}$), aryl ($C_6H_5$, $C_6H_5CH_2$), alkenyl ($CH_2=CH-$) or $-H$ groups and bearing as terminal moiety a reactive group (OH, H, vinyl and the like) or a monofunctional group [$(CH_3)_3SiO$, $(CH_3)_2(CH_2=CH)SiO-$ and the like].

The layers A and $B_n$ (wherein n is suitably 1 to 5) are silicone rubber matrices one layered on the other with various active ingredient content, e.g. 0 to 20%, with the proviso that at least one layer contains active ingredient. Any catalyst providing cross-linking through condensation (suitably the T-5 product of Wacker Co., FRG) may be used as polycondensation catalyst in an amount of 0.01 to 15%, suitably 5 to 8%. Various noble metal salts or noble metal complexes may be used as polyaddition catalysts in an amount of 1 to 100 ppm. This process can be carried out at a wide temperature range, from 15° to 140° C., suitably between 20° C. and 40° C., depending on the properties of the incorporated active ingredient. This process is useful for both the batch or continuous production of the pharmaceutical formulation according to the invention.

According to a preferred embodiment of the invention, a pharmaceutical formulation is prepared which is a multilaminated system built up from silicone rubber layers of various layer thickness and with various active ingredient content. This system is provided with a suitable water-impermeable layer, conveniently with an aluminum foil layer, over the silicone rubber layers and with an adhesive layer ensuring the sticking to the skin surface. The first layer of 0.1 to 3 mm in thickness of the pharmaceutical formulation, which adheres to the skin surface and contains no active ingredient (signed by "A" in FIG. 1), is closely built together with the subsequent layers of various active ingredient content and thus, the zero order dissolution kinetics of the active ingredient is provided by the whole laminated system.

In the compositions according to the invention quite different drugs, e.g. cardiovascular, spasmolytic, anorectogenic, antidiabetic agents as well as drugs affecting the hormone system may be used as active ingredients.

According to the invention, the multilaminated system is formed by polymerizing the individual layers one by one on the surface of each other and one after the other in time.

Depending from the active ingredient of the system, the layer A can be produced by polycondensation in various layer thickness, e.g. 0.1 to 3 mm, at various temperatures, e.g. between 15° C. and 90° C., suitably at 25° to 60° C., of a mixture prepared from e.g. various polydimethylsiloxane-α, ω-diols (hereinafter abbreviated: PDSD), suitably from the Silorol R-1, R-5 and R-30 products of Finomvegyszer Szövetkezet Co., Budapest, Hungary, or from the mixtures thereof, by using various (polycondensation involving) cross-linking catalysts (hereinafter abbreviated: CLC) in an amount of 0.1 to 15%, suitably 5 to 10%. A trifunctional methylsilane derivative containing Si-N and/or Si-O bond, conveniently methyltricyclohexyl-aminosilane, can be used as catalyst or main component; a tetraalkoxysilane, suitably tetraethoxysilane, tetramethoxysilane or the like are used as main-components; and a catalyst mixture containing a dialkyltin salt of a long-chain fatty acid, suitably dibutyltin laurate is employed as initiator. In the case of polysiloxane polymers containing alkyl ($C_nH_{2n+1}$), aryl ($C_6H_5$, $C_6H_5CH_2$), alkenyl ($CH_2=CH-$) or $-H$ groups and bearing a reactive group (OH, H, vinyl and the like) or a monofunctional grouping [$(CH_3)_3SiO$, $(CH_3)_2(CH_2=CH)SiO-$ or the like] as a terminal moiety (hereinafter abbreviated: PSP) the process is carried out in such a way that the layer thickness of the layer A, resulting from the polyaddition under the effect of noble metal salts or noble metal complexes (hereinafter abbreviated: NM type catalysts) used as catalysts and being present in an amount of 1 to 100 ppm, will be 0.1 to 3 mm and the polyaddition process is performed at a temperature between 15° C. and 140° C.

The first layer $B_1$ containing an active ingredient is applied onto the layer A thus prepared. The layer $B_1$ can suitably be prepared by polymerizing at various temperatures, at 15° to 140° C., suitably at 15° to 50° C., a homogenised mixture prepared from the active ingredient as such or from a dilution thereof with a solid or liquid diluent, e.g. lactose, glucose, Aerosil and the like, and from the PDSD or PSP basic material used in varying amounts, e.g. from 0.5 to 20% suitably from 0.5 to 4%, with a CLC or NM type catalyst. When the layer $B_1$ is formed by polycondensation, the amount of a CLC type catalyst may preferably amount to 0.1 to 15%, suitably 5 to 10%, and the preferred temperature may be 15° to 90° C., suitably 20° to 50° C.

When using the polyaddition process, the amount of a NM type catalyst may be 1 to 100 ppm and the process may be carried out at a temperature between 15° C. and 140° C., suitably at 20° to 60° C.

Depending from the nature and properties of the active ingredient, the layers $B_n$ are applied onto the polymerized layers $B_{n-1}$ by repeating the process described hereinabove with a successively increasing active ingredient content between 15% and 25%, differing from the active ingredient content of the layer $B_{n-1}$.

Onto the last layer $B_n$, PDSD or PSP basic material, suitably in a thickness of 0.1 to 1 mm and containing no active ingredient and 0.1 to 15%, suitably 5 to 8%, of a CLC type catalyst or 1 to 100 ppm, suitably 20 ppm, of a NM type catalyst, is applied, and after the attachment of the water-impermeable layer, suitably aluminum foil, the polymerization is carried out at a temperature between 15° C. and 140° C., suitably at 25° to 50° C. Finally, the adhesive layer providing the sticking to the skin of the formulation, is bound to the water-impermeable layer.

More specifically, the present invention presents a pharmaceutical formulation for application to the skin of a patient and useful for the transdermal administration with zero order kinetics of an active ingredient comprising (i) a silicon rubber polymer matrix of laminar structure, (ii) a water-impermeable layer on the side of the laminar structure opposite to the dermal side and (iii) an adhesive layer on the dermal side ensuring fixation to the skin surface, wherein the matrix comprises at least 2 and at most 6 layers being superposed on the surface of each other and where the layers contain different but, compared to the first layer on the dermal side, steadily increasing amounts of the active ingredient, this amount being up to 25% by weight, and, 0 to 45% by weight of one of more pharmacologically acceptable adjuvants, and the individual layers of said matrix are formed from at least one polymer from the following:

(a) alkylpolysiloxane—α, ω-diols having a viscosity of 500 to 100,000 mPas and mixtures of such diols of various polycondensation ratios or (b) polysiloxane polymers and mixtures thereof, these polymers optionally containing substituents of the following groups: alkyl, aryl, aralkyl, alkenyl or H groups and having terminal moieties which are selected from reactive groups or monofunctional groups.

A further formulation of the type just mentioned involves polysiloxane polymers of (b) having substituents such as $C_nH_{2n+1}$, $C_6H_5$, $C_6H_5CH_2$, or $CH_2=CH$ groups and/or terminal groups such as H,OH, vinyl, $(CH_3)_3SiO$ or $(CH_3)_2(CH_2=CH)SiO$ groups.

This formulation can have layers which are 0.1 to 3 mm thick.

The adjuvant can be chosen from lactose, glucose or colloidal silicon dioxide.

The present invention also provides a process for the preparation of a pharmaceutical formulation for application to the skin of a patient and useful for the transdermal administration with zero order kinetics of an active ingredient wherein said process comprises the steps of (1) homogenizing, based on the weight of one layer, up to 25% by weight of an active ingredient compatible with silicone rubber polymers, 0 to 45% by weight of at least one pharmacologically acceptable adjuvant, 0.001 to 15% by weight of a catalyst and 45 to 99.999% by weight of a polymer selected from (a) alkylpolysiloxane—α,ω-diols having a viscosity of 500 to 100,000 mPas and mixtures thereof and (b) polysiloxane polymers and mixtures thereof, said polymers optionally containing substituents selected from alkyl, aryl, aralkyl, alkenyl or H groups and having terminal moieties selected from reactive groups or monofunctional groups;

(2) forming a silicone rubber polymer matrix of laminar structure from mixture (a) by polycondensation or from mixture (b) by polyaddition, at 15° to 150° C., the matrix comprising at least 2 and at most 6 layers being superposed on the surface of each other and those layers containing different but, compared to the first layer on the dermal side, gradually increasing amounts of the active agent, and (3) simultaneously with the formation of the last active ingredient-containing layer, covering the last layer of the laminar structure opposite to the dermal side with a water impermeable layer and covering the water impermeable layer with an adhesive element ensuring fixation of the laminar structure to the skin surface.

The process may also involve forming layers of 0.1 to 3 mm.

The process also involves introducing to the individual layers the active ingredient as such or in the form of a mixture of the active ingredient with one or more various solid or liquid diluents.

A noble metal salt or complex may be used as catalyst of the polyaddition.

The formulations according to the invention were investigated in in vitro studies involving the determination of the active ingredient release during the time unit (mg/h), the rate of dissolution of the active ingredient (mg/cm$^2$/h) as well as the percentage of dissolution of the total active ingredient content.

The dissolution was followed in a Keshary-Chien type diffusion cell [c.f. Drug Development Industrial Pharmacy 10 (6), pp. 883-913, 1984]. In these measurements the sample surface was 3.14 cm$^2$; the liquid was an isotonic sodium chloride solution with a volume of 10 ml and with a temperature of 37° C. The volume of the sample was 1 ml.

The active ingredient content of the samples was determined by measuring the UV extinction by using a VSU 2-P device; Carl Zeiss Jena, GDR. Nitroglycerin was measured at 207 nm in a layer thickness of 2 mm against an isotonic sodium chloride solution. Isosorbide dinitrate was determined at 220 nm in a layer thickness of 2 mm against distilled water.

It can be stated as a conclusion that, under the experimental conditions used, the formulations according to the invention show uniform release of the active ingredient within about 24 hours.

The results of the dissolution studies are illustrated in the graphs 1 and 2.

The short-time stability of the formulations was also studied. Since nitroglycerin used as active ingredient is a volatile substance, the nitroglycerin content of the nitroglycerin-lactose trituration should continuously be controlled. The formulations were stored as packaged in aluminum foil at +5° C. or +30° C. and examined in regular intervals. It was stated that the formulations according to the invention could be stored without any change both at +5° C. and +30° C. as well. The experimental results obtained with the formulation of Example 1 containing nitroglycerin are illustrated in Tables 1 and 2.

TABLE 1

| | (Storage at +30° C.) | | | |
|---|---|---|---|---|
| | day 1 | day 7 | day 21 | day 60 |
| Average dissolution mg/cm$^2$/h | $6.63 \cdot 10^{-5}$ | $7.3 \cdot 10^{-5}$ | $6.61 \cdot 10^{-5}$ | $6.82 \cdot 10^{-5}$ |
| Stanard deviation of the data | $2.29 \cdot 10^{-5}$ | $2.7 \cdot 10^{-5}$ | $1.47 \cdot 10^{-5}$ | $2.09 \cdot 10^{-5}$ |
| Mean deviation | $9.3 \cdot 10^{-6}$ | $1.05 \cdot 10^{-5}$ | $6.01 \cdot 10^{-6}$ | $8.6 \cdot 10^{-6}$ |

TABLE 2

| | (Storage at +5° C.) | | | |
|---|---|---|---|---|
| | day 1 | day 7 | day 21 | day 60 |
| Average dissolution mg/cm$^2$/h | $8.61 \cdot 10^{-5}$ | $8.9 \cdot 10^{-5}$ | $9.19 \cdot 10^{-5}$ | $8.8 \cdot 10^{-5}$ |
| Standard deviation of the data | $2.1 \cdot 10^{-5}$ | $2.9 \cdot 10^{-5}$ | $2.5 \cdot 10^{-5}$ | 2.08 |
| Mean deviation | $8.9 \cdot 10^{-6}$ | $8.5 \cdot 10^{-6}$ | $1.03 \cdot 10^{-5}$ | 8.51 |

When compared to the formulations of the prior art, the formulation according to the invention shows the following advantages.

The building-up of the formulation makes possible the preparation of any transdermally absorbeable pharmaceutical composition as well as a uniform therapeutic blood level of the active ingredient for a longer period, suitably for 18 to 24 hours.

The silicone rubbers employed as basic materials are cheap and physiologically inert to the living organism and do not go into any interaction with the incorporated active ingredient.

The zero order kinetics of the dissolution of the active ingredient can be ensured by the suitable selection of the basic materials used, their layer thickness and the active ingredient content of the individual layers.

No porous or microporous membranes requiring a particular basic material or a specific construction are needed to regulate the dissolution of the active ingredient.

The adhesion of the individual layers to each other and thus, the ensuring of an appropriate structure can easily be satisfied since the layers are essentially identical from the chemical point of view.

The invention is illustrated in detail by the following non-limiting Examples.

EXAMPLE 1

(a)

A mixture containing 60% of dimethylpolysiloxane-α, ω-diol with a viscosity of 50,000 mPa.s and 35% of the same material with a viscosity of 1,000 mPa.s is homogenized under vigorous stirring for 2 minutes, then 5% of Wacker T-5 catalyst are added to the polymeric mixture and the stirring is continued for additional 2 minutes. The homogeneous mixture thus obtained is stretched out in a layer thickness of 0.5 mm in a suitable equipment and cross-linked at 40° C. for 3 hours (layer A).

(b)

A mixture containing 50% of dimethylpolysiloxane-α, ω-diol with a viscosity of 5,000 mPa.s and 25% of the same material with a viscosity of 1,000 mPa.s is homogenized under vigorous stirring for 2 minutes, then 20% of a lactrose-trituration containing 10% of nitroglycerin are portionwise added, the mixture is slowly stirred for 5 minutes and then, after adding 5% of Wacker T-5 catalyst, the homogenisation is continued for additional 5 minutes. The mass obtained is stretched out in a layer thickness of 0.5 mm onto the layer A in a suitable equipment and then cross-linked at 40° C. for 3 hours (layer B$_1$).

(c)

By using the process described under (b) and applying as components 35% of dimethylpolysiloxane-α, ω-diol with a viscosity of 5,000 mPa.s, 20% of the same material with a viscosity of 1,000 mPa.s, 40% of a lactose-trituration containing 10% of nitroglycerin and 5% of Wacker T-5 catalyst onto the layers A+B$_1$ in a thickness of 1 mm, the layer B$_2$ is cross-linked at 40° C. for 3 hours.

(d)

A homogeneous mixture prepared by the process described under (b) from 30% of dimethylpolysiloxane-α, ω-diol with a viscosity of 5,000 mPa.s, 15% of the same material with 1,000 mPa.s as well as from 50% of a lactose-trituration containing 10% of nitroglycerin and 5% of Wacker T-5 catalyst is applied in a thickness of 1 mm onto the surface of the laminated matrix A+B$_1$+B$_2$ and then cross-linked at 40° C. for 3 hours, giving layer B$_3$.

(e)

A layer consisting of 95% of dimethylpolysiloxane-α,ω,-diol with a viscosity of 1,000 mPa.s and 5% of Wacker T-5 catalyst is applied in a thickness of 0.1 mm onto the layer $B_3$ of the laminated matrix consisting of the layers $A+B_1+B_2+B_3$ and then covered by a thin aluminum foil and cross-linked at 40° C. for 3 hours.

(f)

An adhesive textile layer is applied onto the aluminum foil layer which reaches beyond the polymeric metrix and ensures the sticking to the skin of the formulation.

EXAMPLE 2

The layers are built up in the succession of operations described in Example 1, except that:

(a)

The thickness of the layer A is 1 mm and it contains 50% of dimethylpolysiloxane-α,ω-diol with a viscosity of 50,000 mPa.s, 45% of the same with a viscosity of 5,000 mPa.s as well as 5% of Wacker T-5 catalyst. The polymerization is carried out at 60° C. for 90 minutes.

(b)

The thickness of the layer $B_1$ is 1 mm and it contains 70% of a dimethylpolysiloxane-α,ω-diol with a viscosity of 50,000 mPa.s and 20% of the same material with a viscosity of 5,000 mPa.s, as well as 5% of Phenobarbital sodium and 5% of Wacker T-5 catalyst. The polymerization is carried out at 40° C. for 3 hours.

(c)

The thickness of the layer $B_2$ is 1 mm and it contains 70% of dimethylpolysiloxane-α,ω-diol with a viscosity of 50,000 mPa.s, 17% of the same material with a viscosity of 5,000 mPa.s, 8% of Phenobarbital sodium as well as 5% of Wacker T-5 catalyst. The polymerization is carried out at 40° C. for 3 hours.

(d)

The thickness of the layer $B_3$ is 1 mm and it contains 70% of dimethylpolysiloxane-α,ω-diol with a viscosity of 50,000 mPa.s, 13% of the same material with a viscosity of 5,000 mPa.s, 12% of Phenobarbital sodium and 5% of Wacker T-5 catalyst. The polymerization is carried out at 40° C. for 3 hours.

The layers C and D are prepared as described under e) and f) of Example 1.

EXAMPLE 3

The layers are built up in the succession of operations described in Example 1, except that:

(a)

The thickness of the layer A is 1 mm and it contains Wacker 3003/50 type two-component silicone rubber (able for polyaddition) as basic material, the components A and B of which are homogenized in a ratio of 50% : 50%. The polymerization is carried out at 70° C. for 25 minutes.

(b)

The thickness of the layer $B_1$ is 1 mm and it contains 35% of dimethylpolysiloxane-α,ω-diol with a viscosity of 50,000 mPa.s, 40% of the same material with a viscosity of 5,000 mPa.s, 20% of a lactose-trituration containing 40% of isosorbide dinitrate as active ingredient as well as 5% of Wacker T-5 catalyst. The polymerization is carried out at 40° C. for 3 hours.

(c)

The thickness of the layer $B_2$ is 0.5 mm and it contains 25% dimethylpolysiloxane-α,ω-diol with a viscosity of 50,000 mPa.s, 30% of the same material with a viscosity of 5,000 mPa.s, 40% of a lactose-trituration containing 40% of isosorbide dinitrate as active ingredient as well as 5% of Wacker T-5 catalyst. The polymerization is carried out at 40° C. for 3 hours.

(d)

The thickness of the layer $B_3$ is 0.5 mm and it contains 20% of dimethylpolysiloxane-α,ω-diol with a viscosity of 50,000 mPa.s, 30% of the same material with a viscosity of 5,000 mPa.s, 45% of a lactose-trituration containing 40% of isosorbide dinitrate as active ingredient as well as 5% of Wacker T-5 catalyst. The polymerization is carried out at 40° C. for 3 hours.

The layers C and D are prepared as described under e) and f) of Example 1.

EXAMPLE 4

The layers are built up in the succession of operations described in Example 1, except that:

(a)

The thickness of the layer A is 0.25 mm and it contains Wacker 3003/50 type two-component silicone rubber as basic material, the components A and B of which are homogenized in a ratio of 50% : 50%. The polymerization is carried out at 70° C. for 30 minutes.

(b)

The layer $B_1$ contains Wacker 3003/50 type two-component silicone rubber as basic material, the components A and B of which are homogenized in a ratio of 35 : 35% and then 30% of pulverized O-acetylsalicylic acid are added. At the end of the homogenization process it is stretched out onto the layer A in a layer thickness of 1.5 mm. The polymerization is carried out at 50° C. for 1 hour.

(c)

The thickness of the layer $B_2$ is 1.5 mm and it contains the components A and B of the Wacker 3003/50 type silicon rubber basic material in a ratio of 30% : 30% and 40% of pulverized O-acetylsalicylic acid. The polymerization is carried out at 50° C. for 1 hours.

The layers C and D are prepared as described under (e) and (f) of Example 1.

The catalyst (suitably a platinum complex compound) required to the polyaddition processes of Examples 3 and 4 is contained in one of the components of the silicone rubber manufactured industrially, by Wacker.

We claim:

1. A pharmaceutical formulation for application to the skin of a patient and useful and useful for the transdermal administration with zero order kinetics of an active ingredient comprising
    (i) a silicon rubber polymer matrix of laminar structure,
    (ii) a water-impermeable layer adjacent the side of the laminar structure opposite to the dermal side and
    (iii) an adhesive overlay adjacent the water-impermeable layer and extending to the dermal side ensuring fixation to the skin surface, wherein
    said matrix comprises at least 2 and at most 6 layers being superposed on the surface of each other and the layers contain different but, compared to the first layer on the dermal side, steadily increasing amounts of the active ingredient, this amount being up to 25% by weight, and 0 to 45% by weight of one or more pharmacologically acceptable adjuvants, and the individual layers of said matrix are formed from at least one polymer selected from the group consisting of (a) alkylpolysiloxane -$\alpha,\omega$-diols having a viscosity of 500 to 100,000 mPas and mixtures of such diols of various polycondensation ratios and (b) polysiloxane polymers and mixtures thereof, said polymers optionally containing substituents selected from the group consisting of: alkyl, aryl, aralkyl, alkenyl and H groups and having terminal moieties selected from the group consisting of reactive groups and monofunctional groups.

2. A formulation as claimed in claim 1, wherein the polysiloxane polymers of (b) have substituents selected from the group consisting of $C_nH_{2n+1}$, $C_6H_5$, $C_6H_5CH_2$, and $CH_2=CH$ groups and terminal groups selected from the group consisting of H, OH, vinyl, $(CH_3)_3SiO$ and $(CH_3)_2(CH_2=CH)SiO$ groups.

3. The formulation as claimed in claim 1 wherein said layers are 0.1 to 3 mm thick.

4. The formulation as claimed in claim 1 wherein said adjuvant is selected from the group consisting of lactose, glucose and colloidal silicon dioxide.

5. A process for the preparation of a pharmaceutical formulation for application to the skin of a patient and useful for the transdermal administration with zero order kinetics of an active ingredient wherein said process comprises the steps of (1) homogenizing, based on the weight of one layer, up to 25% by weight of an active ingredient compatible with silicon rubber polymers, 0 to 45% by weight of at least one pharmacologically acceptable adjuvants, 0.001 to 15% by weight of a catalyst and 45 to 99.999% by weight of a polymer selected from the group consisting of (a) alkylpolysiloxane-$\alpha, \omega$-diols having a viscosity of 500 to 100,000 mPas and mixtures thereof and (b) polysiloxane polymers and mixtures thereof, said polymers optionally containing substituents selected from the group consisting of alkyl, aryl, aralkyl, alkenyl and H groups and having terminal moieties selected from the group consisting of reactive groups and monofunctional groups, (2) forming a silicone rubber polymer matrix of laminar structure from mixture (a) by polycondensation or from mixture (b) by polyaddition, at 15° to 140° C., said matrix comprising at least 2 and at most 6 layers being superposed on the surface of each other and said layers containing different but, compared to the first layer on the dermal side, gradually increasing amounts of the active agent, and (3) simultaneously with the formation of the last active ingredient-containing layer, covering the last layer of the laminar structure opposite to the dermal side with a water impermeable layer and covering said water impermeable layer with an adhesive element ensuring fixation of the laminar structure to the skin surface.

6. The process as claimed in claim 5 which comprises forming layers of 0.1 to 3 mm.

7. The process as claimed in claim 5 which comprises introducing to the individual layers the active ingredient as such or in the form of a mixture of the active ingredient with one or more various solid or liquid diluents.

8. The process as claimed in claim 5 which comprises using a noble metal salt or complex as catalyst of the polyaddition.

* * * * *